United States Patent
Dijkstra et al.

(10) Patent No.: US 11,918,270 B2
(45) Date of Patent: Mar. 5, 2024

(54) ELECTROSURGICAL GENERATOR, ELECTROSURGICAL SYSTEM, AND METHOD OF OPERATING AN ELECTROSURGICAL GENERATOR

(71) Applicant: OLYMPUS WINTER & IBE GMBH, Hamburg (DE)

(72) Inventors: Jelle Dijkstra, Berlin (DE); Veronika Handrick, Berlin (DE); Andreas Karrasch, Berlin (DE); Frank Breitsprecher, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 306 days.

(21) Appl. No.: 17/216,091

(22) Filed: Mar. 29, 2021

(65) Prior Publication Data
US 2021/0298811 A1    Sep. 30, 2021

(30) Foreign Application Priority Data

Mar. 27, 2020  (DE) .......................... 102020108614.8

(51) Int. Cl.
*A61B 18/12*    (2006.01)
*A61B 18/04*    (2006.01)
(Continued)

(52) U.S. Cl.
CPC ........ *A61B 18/042* (2013.01); *A61B 18/1206* (2013.01); *A61B 18/16* (2013.01);
(Continued)

(58) Field of Classification Search
CPC ............. A61B 18/1206; A61B 18/042; A61B 2018/00601; A61B 2018/00625;
(Continued)

(56) References Cited

U.S. PATENT DOCUMENTS 10,285,750 B2   5/2019   Coulson et al.
11,376,059 B2   7/2022   Fähsing
(Continued)

FOREIGN PATENT DOCUMENTS

CN      1750794 A      3/2006
CN    104337567 A      2/2015
(Continued)

OTHER PUBLICATIONS

Aug. 6, 2021 Extended Search Report issued in European Patent Application No. 21165392.8.
(Continued)

*Primary Examiner* — Michael F Peffley
*Assistant Examiner* — Samantha M Good
(74) *Attorney, Agent, or Firm* — Oliff PLC

(57) ABSTRACT

An electrosurgical generator supplies, during operation, a high-frequency alternating current to an electrosurgical instrument for plasma cutting of body tissue. The electrosurgical generator has outputs for connecting an electrosurgical instrument to supply an electrosurgical instrument connected to the outputs with a high-frequency alternating current, and for determining the impedance of a load connected to the outputs. The electrosurgical generator features impedance and voltage measuring units as well as an output voltage control unit. The output voltage control unit is designed to control the AC output voltage depending on a maximum output voltage value that is set during operation depending on an output value of the impedance measuring unit and/or depending on an output value of the voltage measuring unit, such that the maximum output voltage value predefines a lower AC output voltage during a vaporization phase than during an ignition phase occurring subsequently to the vaporization phase.

15 Claims, 8 Drawing Sheets

(51) Int. Cl.
  *A61B 18/16* (2006.01)
  *G05F 1/12* (2006.01)
  *H03K 5/003* (2006.01)
  *A61B 18/00* (2006.01)
  *A61B 18/14* (2006.01)

(52) U.S. Cl.
  CPC .............. *G05F 1/12* (2013.01); *H03K 5/003* (2013.01); *A61B 2018/00601* (2013.01); *A61B 2018/00625* (2013.01); *A61B 2018/00678* (2013.01); *A61B 2018/00767* (2013.01); *A61B 2018/00833* (2013.01); *A61B 2018/00875* (2013.01); *A61B 2018/00892* (2013.01); *A61B 2018/1407* (2013.01)

(58) Field of Classification Search
  CPC ........... A61B 2018/00767; A61B 2018/00892; A61B 2018/00875; A61B 2018/00678; A61B 2018/00833
  See application file for complete search history.

(56) References Cited

U.S. PATENT DOCUMENTS

| | | |
|---|---|---|
| 2003/0040744 A1 | 2/2003 | Latterell et al. |
| 2004/0019351 A1 | 1/2004 | Ohyama et al. |
| 2007/0173808 A1 | 7/2007 | Goble |
| 2013/0325002 A1 | 12/2013 | Strauss et al. |
| 2013/0325380 A1* | 12/2013 | Behnke, II ............. G01R 27/28 323/285 |
| 2014/0236142 A1* | 8/2014 | Ward ................. A61B 18/1206 606/38 |
| 2015/0272657 A1 | 10/2015 | Yates et al. |
| 2016/0074091 A1 | 3/2016 | Amoah et al. |
| 2017/0325875 A1* | 11/2017 | Assmus ............. A61B 17/3476 |
| 2018/0280071 A1 | 10/2018 | Nold et al. |
| 2018/0360522 A1 | 12/2018 | Winter et al. |
| 2019/0206656 A1 | 7/2019 | Diener |

FOREIGN PATENT DOCUMENTS

| | | |
|---|---|---|
| CN | 108463180 A | 8/2018 |
| CN | 109496142 A | 3/2019 |
| CN | 109804452 A | 5/2019 |
| DE | 198 27 318 B4 | 1/2007 |
| DE | 603 14 184 T2 | 1/2008 |
| DE | 10 2011 005 067 A1 | 9/2012 |
| DE | 10 2017 106 747 A1 | 10/2018 |
| JP | 2003-305054 A | 10/2003 |
| JP | 2014-158705 A | 9/2014 |
| WO | 2006/038646 A1 | 4/2006 |
| WO | 2008/053532 A1 | 5/2008 |
| WO | 2015/156157 A1 | 10/2015 |

OTHER PUBLICATIONS

Jan. 21, 2021 German Office Action issued in German Patent Application No. 102020108614.8.
Jan. 31, 2022 Office Action issued in Japanese Patent Application No. 2021-053545.
Nov. 3, 2023 Office Action issued in Chinese Patent Application No. 202110324594.1.

* cited by examiner

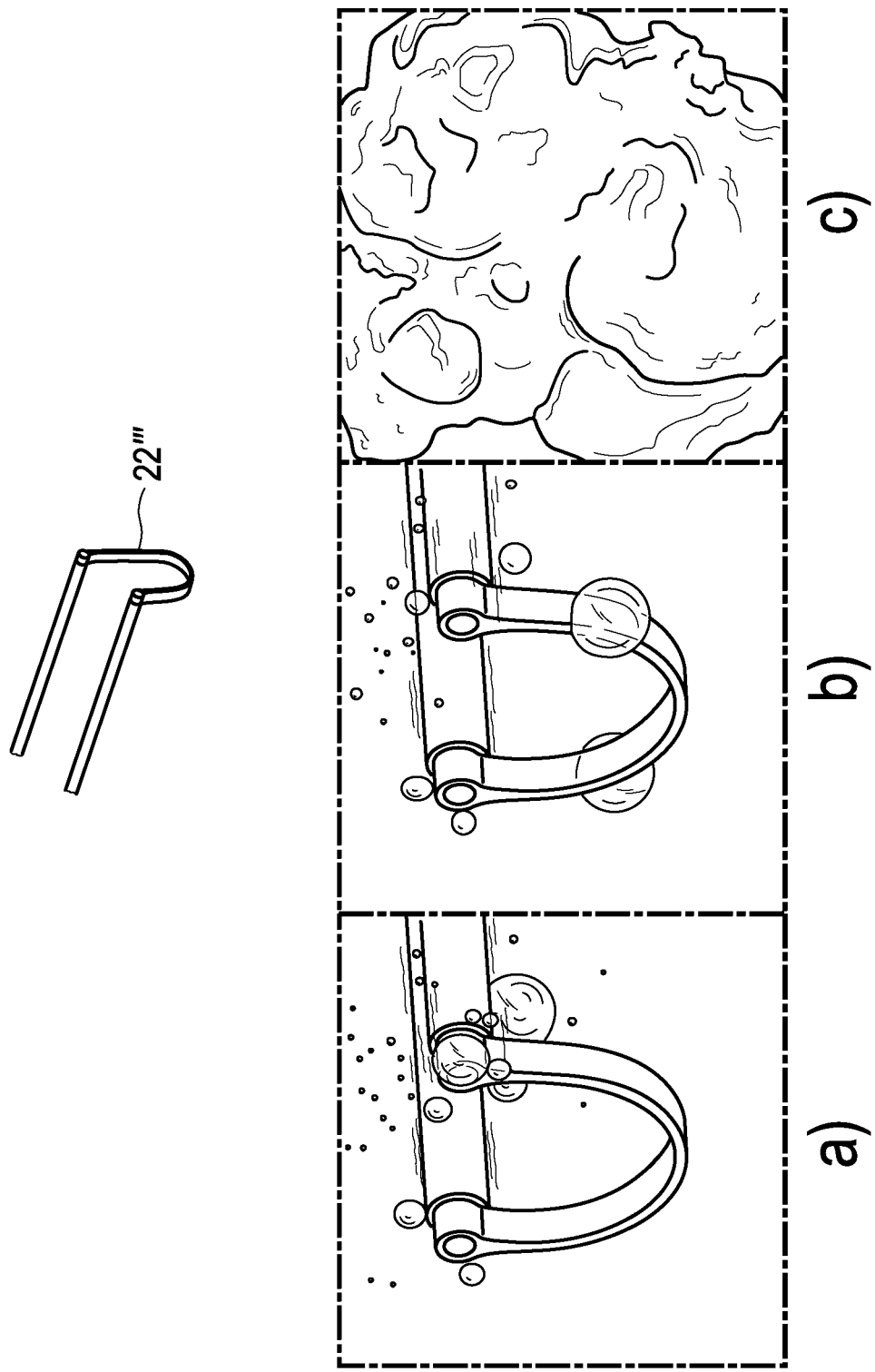

ELECTROSURGICAL GENERATOR, ELECTROSURGICAL SYSTEM, AND METHOD OF OPERATING AN ELECTROSURGICAL GENERATOR

The invention relates to an electrosurgical generator configured to supply high-frequency alternating current to an electrosurgical instrument for plasma cutting of body tissue. The invention also relates to an electrosurgical system comprising an electrosurgical generator and an electrosurgical instrument, as well as a method of operating an electrosurgical generator.

BACKGROUND

Electrosurgery can be used for cutting, coagulating (obliterating) and/or vaporizing biological tissue, i. e. body tissue. High-frequency alternating currents with a frequency between 0.2 MHz and 3 MHz are typically used in electrosurgery.

An electrosurgical system generally comprises an electrosurgical generator for generating the high-frequency alternating current. As a general rule, the electrosurgical generator has two outputs where an electrosurgical instrument can be connected, and a high-frequency AC voltage is provided between these outputs during operation. In addition, an electrosurgical generator generally comprises a high-voltage power supply that generates direct current during operation, and a high-frequency part that is connected to the high-voltage power supply and generates a high-frequency alternating current from the direct current during operation.

Electrosurgical systems are used in urology and gynecology, for example. An electrosurgical generator in combination with a suitable electrosurgical instrument, like a resectoscope, is in particular used for plasma vaporization, for example in the context of TURis (transurethral resection in saline) for the treatment of benign prostate enlargement. The active cutting and vaporizing electrode of this type of electrosurgical instrument is located in an electroconductive rinsing fluid, for example a saline solution (NaCl). The high-frequency AC voltage is used to produce an arc at the active electrode of the electrosurgical instrument (also referred to as plasma ignition).

Body tissue can be vaporized or cut with plasma that is produced in a vapor bubble—i. e. a gas bubble—around an electrode in an electroconductive biocompatible fluid, in particular a saline solution, by producing an arc in a gas volume around an active electrode of the electrosurgical instrument. To this end, a high-frequency AC voltage is applied to the electrode, which generates alternating currents that initially result in evaporation of the saline solution in the immediate vicinity of the active electrode so that a vapor bubble is produced around the electrode. An electric field forms in the vapor bubble between the electrode and the liquid saline solution. If the electric field is strong enough, a gas discharge, also referred to as an arc, occurs due to the ionization of the gas in the vapor bubble, which means plasma (ionized gas) is produced.

In an initial phase, before the plasma and thus an arc is produced, an electroconductive fluid that is present around the electrode has to be vaporized, and an arc subsequently has to be ignited in the produced vapor bubble. This requires that the vapor bubble completely surrounds the electrode and that no electroconductive fluid is present at the electrode since otherwise the strong electric field necessary for ionizing the gas in the vapor bubble cannot be generated, because the direct current flow between the active electrode and the electroconductive fluid prevents the potential difference required for ionization.

After the initial arc ignition—i. e. after the initial plasma formation—a dynamically stable condition is reached wherein, in areas where the gas bubble is at risk of collapsing around the electrode, a particularly strong electric field is generated because of the electroconductive fluid approaching the electrode, which in turn results in particularly strong plasma formation and thus a stronger vaporization of the electroconductive fluid. This causes the gas bubble around the electrode to stabilize.

The initial phase, which is ultimately followed by the phase with a stable plasma arc, thus typically comprises two sub-phases:

In a first sub-phase, also referred to as vaporization phase here, the electroconductive fluid around the active electrode is heated by an electric current and vaporized, so that initially one or several gas bubbles of vapor form around the active electrode until the active electrode is completely surrounded by a layer of gas that finally isolates the active electrode from the electroconductive fluid.

As soon as this is achieved, an arc is ignited in a second sub-phase of the initial phase. This second sub-phase is also referred to as ignition phase here. In the ignition phase, the large drop in voltage across the gas layer between the active electrode and the electroconductive fluid causes the gas in the vapor bubble to be ionized, resulting in the formation of plasma that can be used for cutting or vaporizing tissue. The first ignition of the plasma is difficult and very much dependent on the ambient conditions. In some cases, a stable plasma forms within several milliseconds. Under unfavorable conditions, however, several attempts are required before a stable plasma is ignited.

The different phases and sub-phases before and during plasma ignition also differ with regard to the electrical quantities supplied by the electrosurgical generator.

As long as the active electrode is not or not completely surrounded by a gas layer, impedance between the active electrode and a return electrode is of low resistance. Initially, the impedance is approximately 25 ohms to 50 ohms, depending on the geometry of the electrodes, the temperature of the electroconductive fluid, etc. The output voltage emitted and the power supplied by the electrosurgical generator are thus in phase during this initial heat-up phase of the electroconductive fluid surrounding the active electrode, and they have no DC voltage component.

As soon as vaporization of the electroconductive fluid starts and the surface of the active electrode is partially surrounded by gas, the impedance between the outputs of the electrosurgical generator increases because the surface resistance between the active electrode and the electroconductive fluid increases. However, the surface resistance only contributes to the total impedance between the electrodes—and thus between the outputs of the electrosurgical generator—to a relatively small degree. The impedance during the vaporization phase thus only increases minimally until almost the entire active electrode is surrounded by gas.

As soon as the active electrode is completely surrounded by gas, the vaporization phase ends, and the ignition phase starts. During the ignition phase, ohmic current can no longer flow between the electrodes. The impedance is thus much greater than during the vaporization phase and—theoretically—purely capacitive. Since the impedance of the electroconductive fluid is very low, the electroconductive fluid produces an equipotential shroud around the gas layer.

An electric field forms across the gas layer between the electrode and the electroconductive fluid.

As a result of the no longer occurring current flow, the gas layer around the active electrode gets smaller again because some of the vapor that makes up the gas bubble at the boundary layer between the gas and the electroconductive fluid condenses again. A thinning of the gas layer results in the electric field intensity increasing across the inner gas layer; it can increase so much that it causes the gas in the gas bubble to be ionized and a first arc being produced. The duration of this ignition phase depends on the thickness of the gas layer after the vaporization phase. The duration can be very short—typically in the range of several milliseconds—or even infinitesimally short.

As soon as the electric field across the gas layer is strong enough to cause the gas to ionize, plasma breakdowns—i. e. arcs—occur, resulting in electrical discharge. Since the surface of the active electrode is smaller than the surface of the electroconductive fluid surrounding the gas bubble, the electric field strength is greater on the active electrode side than on the side of the electroconductive fluid. This results in a DC voltage component in the AC output voltage. This DC voltage component (DC offset) is also referred to as "spark voltage" and has approximately 100 volts.

As a result of the electric breakdown (plasma breakdown), the saline solution is vaporized at the boundary layer between the gas and the electroconductive fluid, and the thickness of the gas layer increases again in the area of the plasma breakdown. Thus, whenever the thickness of the gas layer decreases so much again as a result of condensation that the electric field strength increases to the extent that arcing occurs, the thickness of the gas layer will increase again because of the vaporizing electroconductive fluid. This way the thickness of the gas layer around the active electrode is self-stabilizing, and the plasma around the active electrode is in an equilibrium phase. In the equilibrium phase, an equilibrium condition is created in which the thickness of the gas layer is just great enough that the thickness increase as a result of plasma breakdowns offsets the thickness decrease as a result of condensation at the boundary layer between the gas and the saline solution. Thus, in the equilibrium phase, plasma breakdowns will "automatically" occur in areas where the gas layer around the active electrode is thinnest because the electric field strength is at its highest level there. Correspondingly, new gas is produced through vaporization in exactly the area where it is needed. The output voltage of the electrosurgical generator determines the thickness of the gas layer.

According to the state of the art, an AC output voltage between 250 volts and 350 volts, for example 280 volts or 320 volts, is typically preset in electrosurgical generators for plasma cutting.

Problems occasionally occur in practice during plasma ignition for cutting of tissue.

SUMMARY

It is the object of the invention to improve an electrosurgical generator as regards its suitability for plasma cutting of tissue.

According to the invention, this object is achieved with an electrosurgical generator that is configured to emit, when in operation, a high-frequency alternating current to an electrosurgical instrument for plasma cutting of body tissue. The electrosurgical generator has outputs for connecting an electrosurgical instrument to supply an electrosurgical instrument connected to the outputs with high-frequency alternating current.

The electrosurgical generator features an impedance measuring unit to measure the impedance of a load connected to the outputs. In addition, the electrosurgical generator features an output voltage control unit and can comprise a voltage measuring unit.

The output voltage control unit is configured to control an AC output voltage of the electrosurgical generator in accordance with a preset maximum output voltage value.

The impedance measuring unit is designed to measure the impedance of a load at the outputs of the electrosurgical generator. To this end, the impedance measuring unit can be designed to detect a voltage, a current, and/or a phase shift. For example, the impedance measuring unit can measure the impedance from the detected current, the detected voltage, and possibly from the detected phase. The detected phase is important if a current measuring unit and a voltage measuring unit only measure the RMS values of current and voltage because the impedance can be determined just as effectively based on the RMS values of current and voltage as well as phasing, as it can be based on the momentary values of current and voltage.

The voltage measuring unit is designed to detect the voltage at the outputs of the electrosurgical generator, in particular a DC offset in a voltage at the outputs.

The output voltage control unit is designed to control the AC output voltage—in particular its RMS value—in relation to a maximum output voltage value. According to the invention, the predefined maximum output voltage value is different at least for part of the initial phase than it is in the subsequent equilibrium phase.

According to a first aspect of the invention, the predefined maximum output voltage value during the vaporization phase—i. e. at the beginning of the initial phase—is smaller than the maximum output voltage value intended for the actual plasma cutting during the equilibrium phase.

According to a second aspect of the invention, the predefined maximum output voltage value during the ignition phase—i. e. towards the end of the initial phase—is greater than the maximum output voltage value intended for the actual plasma cutting during the equilibrium phase.

Both aspects of the invention can be implemented independently and thus constitute separate inventions. However, both aspects can also be combined, in particular in such a way that the electrosurgical generator is configured to apply a maximum output voltage value for the vaporization phase that is smaller than the maximum output voltage value intended for the equilibrium phase, and to apply a maximum output voltage value for the ignition phase that is greater than the maximum output voltage value intended for the equilibrium phase. Both aspects, individually and in combination with each other, contribute to a more reliable ignition of an arc at the beginning of plasma cutting.

In order to detect the end of the vaporization phase and the start of the ignition phase, or the end of the ignition phase and the start of the equilibrium phase, or both, the output voltage control unit is preferably connected to the impedance measuring unit or the voltage measuring unit, or both.

In order to detect the end of the vaporization phase and the start of the ignition phase, the output voltage control unit can be configured to detect an impedance increase at the outputs of the electrosurgical generator beyond a predefined value. The predefined value can be derived from the impedance measured by the impedance measuring unit at the start of the vaporization phase, for example a predefined multiple of this impedance.

In order to detect the end of the ignition phase and the start of the equilibrium phase, the output voltage control unit can be configured to detect a DC offset in the AC output voltage and to apply the predefined maximum AC output voltage value immediately or after a predefined time interval after detecting a DC offset.

The difference compared to the state of the art is the fact that not just one single maximum AC output voltage value that is suitable for the equilibrium phase and already applied during the initial phase—i. e. the vaporization phase and the ignition phase—is predefined for plasma cutting, but at least one maximum AC output voltage value that is different from the maximum AC output voltage value suitable for the equilibrium phase.

The findings that a maximum AC output voltage value suitable for the equilibrium phase can result in unstable conditions during the initial phase, which could negatively impact a reliable ignition of the plasma, are taken into consideration in this invention.

The output voltage control unit is thus designed to control the AC output voltage depending on a maximum output voltage value that, when in operation, is preset depending on an output value of the impedance measuring unit and/or depending on an output value of the voltage measuring unit (this value serves as the basis for detecting the start and the end of the vaporization and/or ignition phase) such that the maximum output voltage value during a vaporization phase presets a lower AC output voltage than during an ignition phase occurring subsequently to the vaporization phase.

The output voltage control unit is thus configured to use different maximum output voltage values for the initial phase and for the equilibrium phase as its basis. In this context, the initial phase can comprise the vaporization phase and/or the ignition phase, wherein, during the vaporization phase, a direct electrical contact exists between the active electrode and the electroconductive fluid surrounding the active electrode, and the electroconductive fluid is vaporized due to the electrical heating of the electroconductive fluid as a result of current flowing through the electroconductive fluid. During the ignition phase, the active electrode is completely surrounded by the gas bubble produced as a result of vaporization, and the impedance measured by the impedance measuring unit is considerably higher than during the vaporization phase. As soon as the gas in the gas bubble is ionized and an electric arc forms, a DC offset occurs in the alternating current present at the outputs of the electrosurgical generator. This DC offset is detected by the DC voltage measuring unit, which can then generate a corresponding output signal serving as a sign for a (first) electric arc.

During the equilibrium phase, the plasma around the active electrode is stable. The maximum output voltage value, upon which the output voltage control of the electrosurgical generator by the output voltage control unit is based during the equilibrium phase, is typically higher than the maximum output voltage value upon which the output voltage control of the electrosurgical generator by the output voltage control unit is based during the vapor phase.

According to the first aspect of the invention, the maximum output voltage value, upon which the output voltage control of the electrosurgical generator by the output voltage control unit is based during the vaporization phase, is lower than the maximum output voltage value preset for the output voltage control of the electrosurgical generator by the output voltage control unit during the equilibrium phase. A fixed maximum output voltage value is preferably not preset for the vaporization phase, but preferably set based on the impedance measured between the outputs of the electrosurgical generator during the vaporization phase, so that an almost constant current density is achieved at the transition between the active electrode and the saline solution surrounding it.

According to the second aspect of the invention, the maximum output voltage value, upon which the output voltage control of the electrosurgical generator by the output voltage control unit is based during the ignition phase occurring subsequently to the vaporization phase, is higher than the maximum output voltage value preset by the output voltage control unit for the output voltage control of the electrosurgical generator during the equilibrium phase. A higher maximum output voltage value for the ignition phase as compared to the subsequently occurring equilibrium phase results in an increased AC output voltage of the electrosurgical generator during the ignition phase and triggers faster and more reliable plasma ignition.

The findings that, by measuring the output voltage and the output current of the electrosurgical generator, values such as the impedance or a DC offset and thus the differentiation between the different phases of the ignition process can be derived, are taken into consideration in this invention. Detection of the different phases before and during plasma ignition around the active electrode of an electrosurgical instrument makes it possible to preset different maximum output voltage values individually and specifically for each phase instead of setting a fixed maximum output voltage value for all phases.

The output voltage control unit is preferably designed to control the AC output voltage depending on a maximum output voltage value, which is used during operation depending on an output value of the impedance measuring unit for detecting the start of the ignition phase and/or depending on an output value of the voltage measuring unit for detecting the end of the ignition phase, such that the maximum output voltage value is higher during the ignition phase than during an equilibrium phase occurring subsequently to the ignition phase.

The electrosurgical generator is preferably designed to detect the vaporization phase and the start of the ignition phase based on a measured impedance. The electrosurgical generator is preferably designed to apply, as a criterion for the start of the ignition phase, a drop in the current intensity of the AC output current during the vaporization phase to a preset fraction—for example one third—of the current intensity of the AC output current at the start of the vaporization phase. The electrosurgical generator is thus preferably designed to detect the start of the ignition phase when the current intensity of the AC output current during the vaporization phase has dropped to one third or one quarter of the current intensity of the AC output current at the start of the vaporization phase.

According to a further preferred embodiment, the electrosurgical generator is designed to detect the end of the ignition phase based on a DC offset in the voltage present at the outputs of the electrosurgical generator.

The output voltage control unit is preferably designed to apply, during the vaporization phase, a maximum output voltage value updated depending on a respectively current output value of the impedance measuring unit and/or the voltage measuring unit. Updating of the maximum output voltage value is preferably done in such a way that an almost constant current intensity is created at the transition from the active electrode to a fluid present at this active electrode. This means that, when the active electrode is increasingly covered by a vapor bubble during the course of the vaporization phase and the surface of the electrode that comes into contact with the conductive fluid thus decreases, the output voltage control unit reduces the AC output voltage accordingly so that the current intensity remains at least nearly constant.

The electrosurgical generator is preferably designed to determine the impedance between the two outputs of the electrosurgical generator using the impedance measuring unit prior to the start of the vaporization phase, and to set the maximum output voltage value at the start of the vaporization phase such that the current intensity as a result of impedance and output voltage is smaller than a maximum current intensity of the AC output voltage that can be supplied by the electrosurgical generator.

Alternatively, the output voltage control unit can be designed to apply, during the vaporization phase, a maximum output voltage value predefined for the vaporization phase. The predefined maximum output voltage value is chosen in such a way that the maximum current that can be supplied by the electrosurgical generator is also not exceeded during the low impedance occurring at the start of the vaporization phase, in accordance with $U_{max}=Z_{measured}*I_{max}$. Since the impedance Z will only continue to increase during and up to the end of the vaporization phase, the electrosurgical generator can maintain the predefined maximum output voltage because the current will continue to decrease. This variant is easier to implement than a maximum output voltage value updated depending on a respectively current output value of the impedance measuring unit and/or the voltage measuring unit, and it can also prevent an overly strong vapor generation towards the end of the vaporization phase.

The electrosurgical generator is preferably dimensioned in such a way that it can supply a maximum AC output voltage greater than 250 V and a maximum AC output current greater than 4 A, for example a maximum AC output voltage between 250 V and 400 V and a maximum AC output current between 4 A and 12 A.

The invention also proposes an electrosurgical system comprising an electrosurgical generator of the type described herein, and an electrosurgical instrument that is or can be connected to outputs of the electrosurgical generator. The electrosurgical instrument features an active electrode and at least one return electrode as well as at least one fluid line arranged relative to the active electrode in such a way that the active electrode can be surrounded by the electro-conductive fluid during operation.

The active electrode is preferably designed as a loop electrode or a button electrode.

The electrosurgical instrument is preferably a resectoscope.

Another aspect of the invention is a method of operating an electrosurgical generator. A first variant of the method comprises the following steps:
  Generating an AC output voltage and supplying the AC output voltage to outputs of the electrosurgical generator, wherein a maximum AC output voltage value is predefined for the AC output voltage;
  Determining the load present at the outputs and comparing the load with a threshold value, which is defined such that a load falling below this threshold value indicates the occurrence of a vaporization phase;
  Wherein, as long as the load remains below the threshold value, a maximum AC output voltage value is preset that is at least 30% smaller than a maximum output voltage value that is preset when the threshold value is exceeded; and
  Controlling the AC output voltage based on the respectively preset maximum AC output voltage value.

In this context, the maximum AC output voltage value is preferably updated in relation to the specific load in case of a changing load, as long as it remains below the threshold value.

The load can be determined based on an impedance at the outputs of the electrosurgical generator, for example. The threshold value, serving as a criterion for detecting a vaporization phase, is then an impedance value, for example, defining a preset dimension that is preferably derived from an impedance measured by the impedance measuring unit at the start of the vaporization phase. The vaporization phase occurs when the value falls below the threshold value, i. e. if the impedance has not exceeded the preset dimension. The impedance measuring unit measures the impedance e. g. from the detected current, the detected voltage and—if only the RMS values of current and voltage are detected—the phase.

This method can be used to prevent an overly strong vapor formation especially towards the end of the vaporization phase.

Additionally, or alternatively, the method can comprise the following steps:
  Generating an AC output voltage and supplying the AC output voltage to outputs of the electrosurgical generator, wherein a maximum AC output voltage value is predefined for the AC output voltage;
  Determining the load at the outputs (18) and comparing the load with a threshold value, which is selected such that a load falling below this threshold value indicates the occurrence of a vaporization phase.
  Detecting a DC offset in the AC output voltage at the outputs;
  Wherein, as soon as the threshold value is exceeded and no DC offset is detected in the AC output voltage at the outputs (18), a maximum AC output voltage value is preset, which is higher than a maximum output voltage value that is preset if a DC offset is detected; and
  Controlling the AC output voltage based on the maximum AC voltage output value.

Instead of detecting a DC offset, a frequency analysis of the AC output voltage can also be performed to detect the occurrence of an arc. The frequency analysis can comprise a Fourier transform, in particular a Fast Fourier Transform (FFT).

This type of second variant of the method can be used to stabilize an arc after the initial ignition.

The two variants of the method can be combined.

Preferably, the method also comprises a step of detecting the start of an ignition phase based on an impedance increase beyond a threshold value, which is determined based on an initial and a preset impedance value or based on an AC output current decrease below a preset fraction of an initial AC output current value.

BRIEF DESCRIPTION OF THE DRAWINGS

The invention will now be explained in more detail using exemplary embodiments referencing the figures. The figures show the following:

FIGS. 5a)-c): An alternative embodiment of an active electrode for an electrosurgical instrument;

DETAILED DESCRIPTION OF EMBODIMENTS

Figure 1:
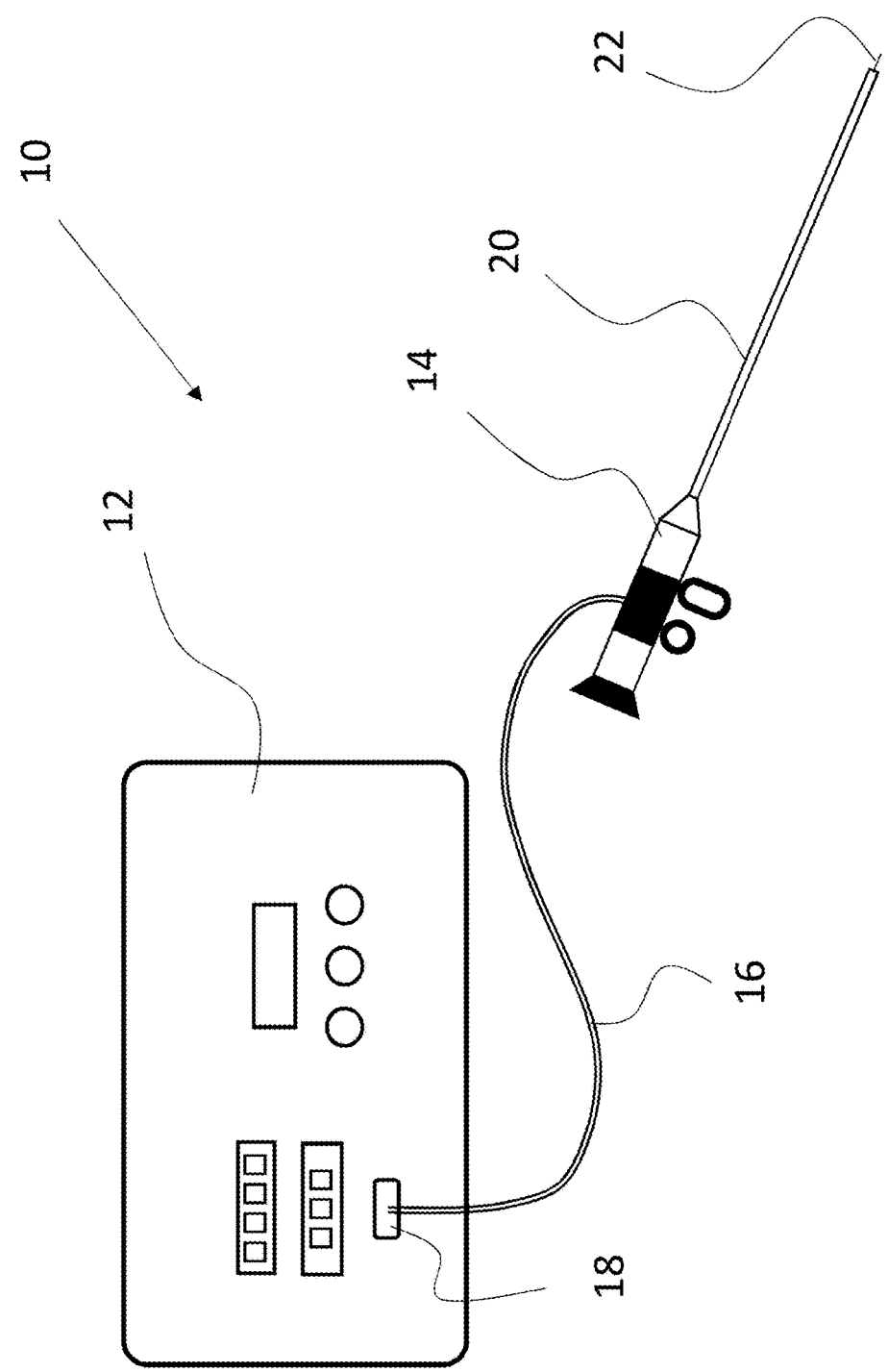
FIG. 1: An electrosurgical system with an electrosurgical generator and an electrosurgical instrument connected thereto.

FIG. 1 shows an electrosurgical system 10. The electrosurgical system 10 comprises an electrosurgical generator 12 and an electrosurgical instrument 14. The electrosurgical instrument 14 is connected to the electrical outputs 18 of the electrosurgical generator 12 with a connection cable 16.

In the displayed exemplary embodiment, the electrosurgical instrument 14 is a resectoscope with a tube 20, through which an electroconductive fluid as the rinsing fluid can be transported to a distal end of the tube 20. A fluid line is provided in the tube 20 for this purpose. The electroconductive fluid circulates and is then drained through the tube 20. The tube 20 thus comprises at least two lumina through which the electroconductive fluid can be transported to the distal end of the tube 20 so that it can exit there, while, at the same time, fluid from the distal end of the tube 20 is drained through another lumen. The lumina thus serve as fluid lines. FIG. 1 does not show the corresponding hose connection points for the electroconductive fluid on the electrosurgical instrument 14.

The active electrode 22 of the electrosurgical instrument 14 can be extended out from the tube 20, as indicated in FIG. 1, or it can be retracted into the tube 20. The electrosurgical instrument 14 typically features a spring so that the active electrode 22 either has to be manually pushed out of the tube 22 against the spring resistance or, reversely, can be manually retracted into the tube 22 against the spring resistance.

The active electrode 22 can have different shapes, for example a button electrode or a loop electrode. FIG. 1 does not show a return electrode, which can be formed by the tube 20, for example, but can also be pushed out of the tube 20 or retracted into it together with the active electrode 22.

Figure 2:
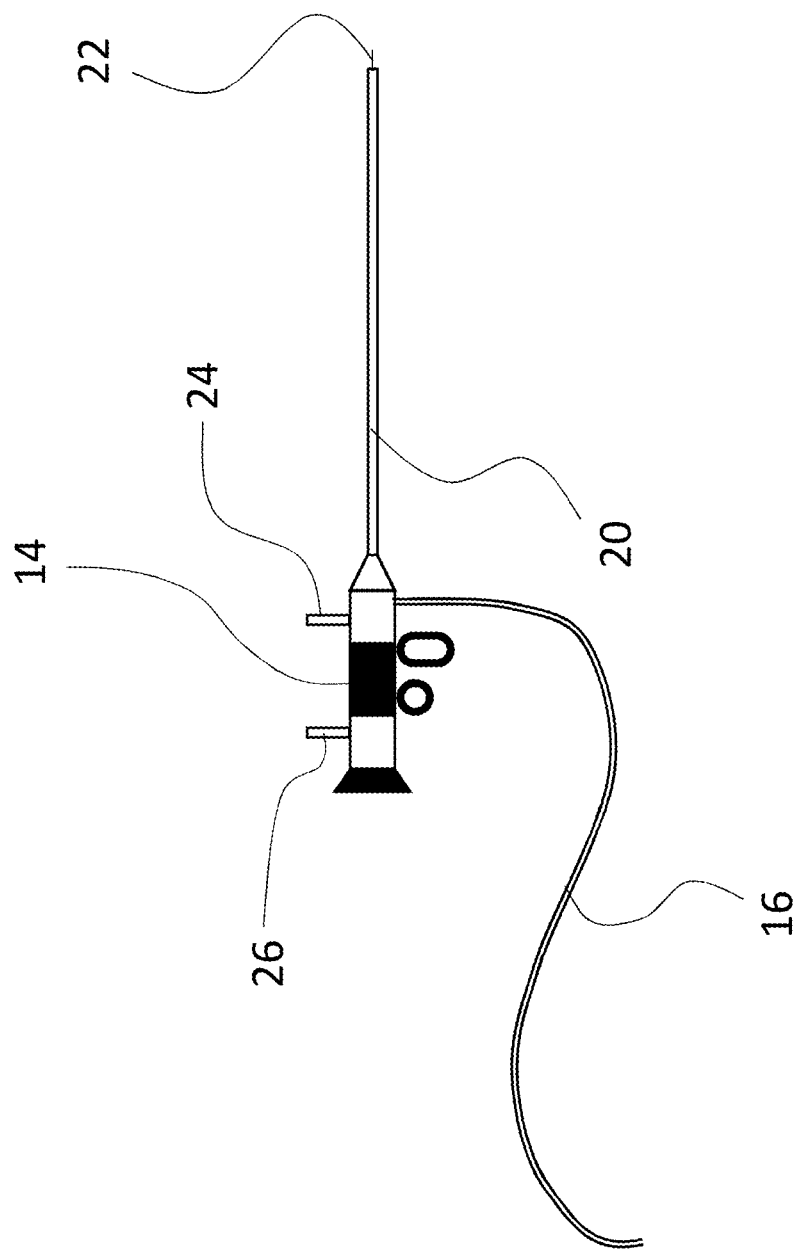
FIG. 2: An illustration of the use of a resectoscope as an electrosurgical instrument.

FIG. 2 shows an electrosurgical instrument 14 in use. FIG. 2 also shows, aside from the connection cable 16, the hoses 24 and 26 used for supplying and draining the electroconductive fluid. An active electrode 22 is extended out from the tube 20 at the distal end of the tube 20 of the electrosurgical instrument 14.

If a high-frequency AC voltage is applied between the active electrode 22 and a corresponding return electrode, this voltage initially causes a current flow through the electroconductive fluid surrounding the active electrode 22. Because of the current flow, the electroconductive fluid around the active electrode 22 heats up and is vaporized as a result. The current flow between the active electrode 22 and the corresponding return electrode through the electroconductive fluid continues until the active electrode 22 is completely surrounded by a vapor bubble. As soon as that happens, an alternating electrical field forms in the produced vapor bubble between the active electrode 22 and the electroconductive fluid surrounding the vapor bubble. When the field strength of the alternating electrical field is high enough, the gas in the vapor bubble around the active electrode 22 is ionized, and a plasma—identifiable by an arc—is produced. The first arc is produced in the area where the vapor bubble around the electroconductive fluid surrounding the active electrode is closest to the active electrode 22, because the field strength of the alternating electrical field is at its highest in that area. The arc thus produced causes additional fluid of the electroconductive fluid to be vaporized so that the vapor bubble around the active electrode 22 does not collapse as a result, but a dynamically stable state of equilibrium forms around the active electrode 22.

Figure 3:
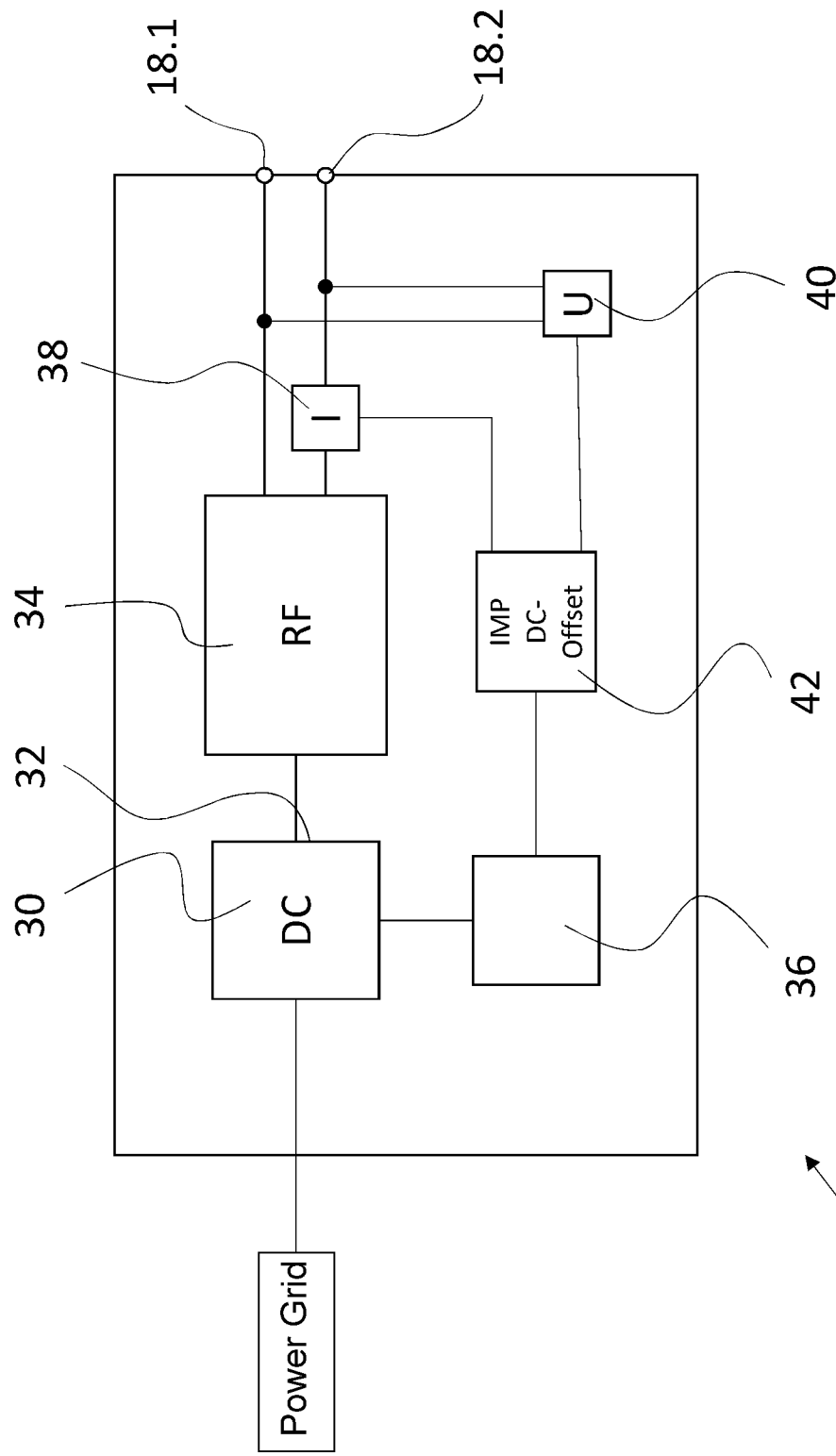
FIG. 3: A schematic diagram of an electrosurgical generator.

The AC voltage required to produce and maintain a plasma around the active electrode 22—and also the alternating current required for vaporizing the electroconductive fluid—are supplied by the electrosurgical generator 12. As shown in FIG. 3, the electrosurgical generator 12 has a high-frequency power supply 30 for this purpose, which can be connected to the usual public power grid and provides a high-frequency direct current at its output 32. This high-frequency direct current is supplied to a high-frequency power supply 34 of the electrosurgical generator 12. The high-frequency power supply 34 of the electrosurgical generator 12 serves as an inverter and produces a high-frequency AC voltage that is supplied to the outputs 18.1 and 18.2 of the electrosurgical generator 12 via an output transformer (not shown) of the high-frequency power supply 34. The electrosurgical instrument 14 can be connected to the outputs 18.1 and 18.2 of the electrosurgical generator 12, as shown in FIG. 1.

To control the output voltage of the electrosurgical generator 12, an output voltage control unit 36 is provided that controls the output voltage at the outputs 18.1 and 18.2 based on a maximum output voltage value such that a preset maximum output voltage value is not exceeded during operation. The invention stipulates that the maximum output voltage value to be respectively applied should be individually preset for the different phases during plasma ignition, while the phases for plasma ignition should be detected based on the electrical output values at the outputs 18.1 and 18.2.

A current measuring unit 38 and a voltage measuring unit 40 are provided for this purpose, which respectively measure the current supplied via the two outputs 18.1 and 18.2 and at the same time the voltage drop at the two outputs 18.1 and 18.2. The output values of the current measuring unit 38 and the voltage measuring unit 40 are supplied to an analysis unit 42 that is configured, on the one hand, to measure the impedance of the load present at the outputs 18.1 and 18.2. In that sense, the analysis unit 42 is an impedance measuring unit. The impedance measuring unit can determine the impedance from the detected current, the detected voltage and possibly the detected phase, for example. The detected phase is important if a current measuring unit and a voltage measuring unit only measure the RMS values of current and voltage, because the impedance can be determined just as well based on the RMS values of current and voltage as well as the phasing as it can be based on the momentary values of current and voltage. On the other hand, the analysis unit 42 is also configured to measure a DC offset in the AC voltage drop at the outputs 18.1 and 18.2. In this sense, the analysis unit 42 also serves as a DC voltage measuring unit. The analysis unit 42 supplies output values to the output voltage control unit 36 based on the measured impedance and the measured DC offset. The output voltage control unit 36 is designed to determine a respective maximum output voltage value, upon which the output voltage control is based, on the basis of the output values for impedance and DC offset supplied by the analysis unit 42.

Control of the output voltage of the electrosurgical generator 12 is thus performed by generating corresponding maximum output voltage values for the output voltage control unit 36.

FIG. 4 is a schematic diagram of the different phases during plasma ignition around an active electrode—in this case a button electrode 22'.

Figure 4A:
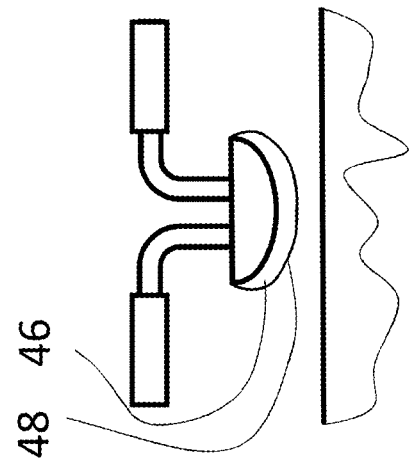
FIGS. 4a)-f): Different phases during plasma ignition around an active electrode of an electrosurgical instrument.
Figure 4B:
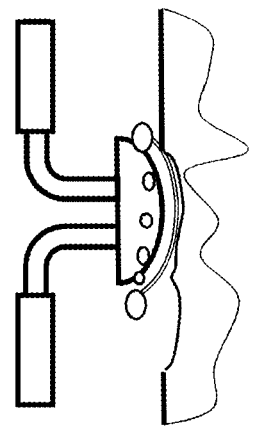
Figure 4C:
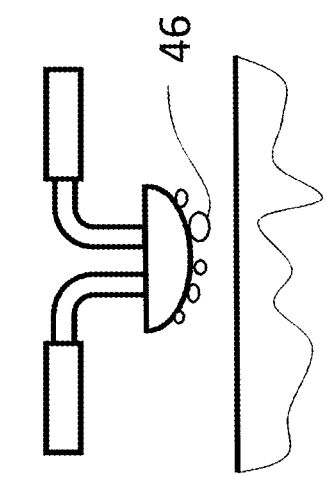

Larger electrodes 44.1 and 44.2 are provided around the supply lines 42 to the active electrode 22' as compared to the active electrode 22'. When in operation, both the active electrode 22' and the return electrodes 44.1 and 44.2 are surrounded by a conductive cooling fluid, namely a saline solution. When a high-frequency AC voltage from the generator 12 is applied between the active electrode 22' and the return electrodes 44.1 and 44.2, an alternating current will first flow through the conductive fluid surrounding the active electrode 22 and the return electrodes 44.1 and 44.2. This is indicated in FIG. 4*a*. The conductive fluid is heated up by the current flow and bubbles 46 form, as indicated in FIG. 4*b*. As soon as the active electrode 22' is completely surrounded by the vapor bubble 46, the direct current flow between the active electrode 22' and the conductive fluid stops. Instead, an alternating electrical field forms between the active electrode 22' on the one side and the boundary layer 48 between the conductive fluid and the vapor bubble 46 on the other side. The thinner the vapor bubble 46 is, the higher the field strength of this alternating electrical field. The electrical field strength is highest in the area where the conductive fluid and/or the boundary layer 48 is closest to the active electrode 22'. FIG. 4*c* shows the fully developed vapor bubble 46.

Figures 4D, 4E, 4F:
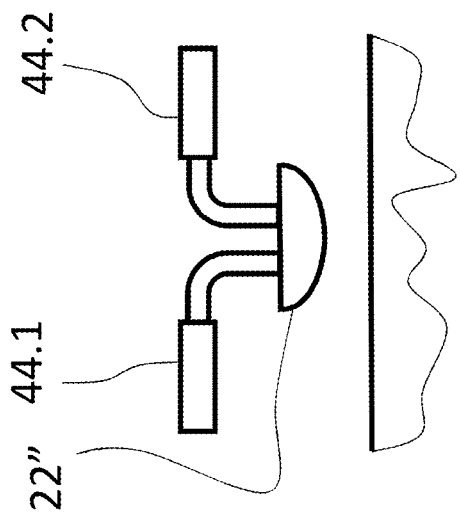

If the electrical field strength between the active electrode 22' and the electroconductive fluid surrounding the vapor bubble 46 exceeds a specific dimension, the gas in the vapor bubble 46 is ionized and plasma 50—recognizable by an arc—forms around the active electrode 22'. As soon as the plasma has been ignited, the active electrode 22 can be moved into the vicinity of biological tissue 50 to be treated, in order to vaporize part of the biological tissue 52 using the plasma 50 and thus partially ablate or cut the biological tissue 52. This is shown in FIGS. 4*d* and 4*e*.

A loop electrode 22" can also be provided as the active electrode for cutting biological tissue as if using a paring knife. This is shown in FIG. 5.

During the vaporization phase, as it is indicated in FIG. 4*b* for example, an increasingly larger part of the active electrode 22 is gradually surrounded by a vapor bubble 46 so that the contact surface between the conductive fluid surrounding the active electrode 22 and the active electrode 22 keeps getting smaller. Since the impedance between the active electrode 22 and the return electrodes 44.1 and 44.2 does not decrease to the same extent as the contact surface between the electroconductive fluid and the active electrode 22, if the output voltage of the electrosurgical generator 12 remains constant, the current density in the electroconductive fluid will increase where it touches the active electrode 22. The reason for this is that the impedance between the active electrode 22 and the return electrodes 44.1 and 44.2 is not determined solely by the contact resistance from the active electrode 22 to the electroconductive fluid, but also by the resistance (or the impedance) of the electroconductive fluid and the contact resistance to the return electrodes 44.1 and 44.2. It can be assumed, for example, that the impedance between the active electrode 22 and the return electrodes 44.1 and 44.2 is initially approximately 25Ω during the vaporization phase (see FIG. 4*a*). These 25Ω are, for example, composed of approximately 10Ω of contact resistance between the active electrode 22 and the electroconductive fluid as well as approximately 15Ω of impedance of the electroconductive fluid (including the contact resistance between the electroconductive fluid and the return electrodes 44.1 and 44.2). In this example, the 15Ω of impedance of the electroconductive fluid can be assumed to be more or less constant and to remain unchanged when the vapor bubble 46 around the active electrode 22 increases in size. However, the contact resistance between the active electrode 22 and the electroconductive fluid increases—and inversely proportional to the degree of coverage at which the vapor bubble covers the active electrode 22. A degree of coverage of 0 means that a vapor bubble has not formed yet and that the electroconductive fluid is in full contact with the active electrode 22. A degree of coverage of 1 means that the active electrode 22 is completely surrounded by a vapor bubble 46. Based on this assumption, the result is that the impedance between the active electrode 22 and the return electrodes 44.1 and 44.2 depends on the degree of coverage in accordance with the following formula:

$$Z = 15\,\Omega + \frac{10\,\Omega}{(1-sc)}$$

wherein Z is the impedance between the active electrode 22 and the return electrodes 44.1 and 44.2, and sc is the degree of coverage at which the vapor bubble 46 covers the surface of the active electrode 22. As already said, a degree of coverage sc=0 means that the electroconductive fluid is in full contact with the surface of the active electrode 22, while a degree of coverage sc=1 means that the surface of the active electrode 22 is completely surrounded by a vapor bubble 46.

As a result, the impedance in the initial stage of the vaporization phase increases only slowly and then increases strongly towards the end of the vaporization phase, for example at a degree of coverage in the range of 0.8 (80%). This kind of impedance increase is also accompanied, at least initially, by an increase in the output voltage because the electrosurgical generator 12 can only supply a limited maximum current, so that the electrosurgical generator 12 cannot reach its maximum output voltage of e. g. 320 V$_{RMS}$ at a lower load impedance. This is indicated as a dotted line in FIG. 6.

The reason for this is that a typical electrosurgical generator 12 can only supply a limited maximum output current of e. g. 4 to 5 A$_{RMS}$ so that a preset maximum output voltage of e. g. 320 V$_{RMS}$ or 350 V$_{RMS}$ cannot be achieved with low impedance values. With an initially low impedance between the active electrode 22 and the return electrodes 44.1 and 44.2—and thus also between the outputs 18.1 and 18.2 of the electrosurgical generator 12—of approximately 25Ω, the limited maximum output current of the electrosurgical generator 12 acts as a limiting value so that the electrosurgical generator 12 cannot supply its maximum output voltage. If this were possible, the electrosurgical generator 12 would supply current of 12.8 $A_{RMS}$ at an output voltage of 320 $V_{RMS}$, if the load is 25Ω.

As the degree of coverage of the active electrode 22 increases, the output voltage of the electrosurgical generator 12 will therefore increase, while the current supplied by the electrosurgical generator 12 remains constant. With an increasing degree of coverage sc, the output voltage, the output power and also the current density at the transition between the active electrode 22 and the electroconductive fluid will thus increase. It is only when the impedance between the active electrode 22 and the return electrodes 44.1 and 44.2 has increased enough as a result of the expanding vapor bubble, so that the electrosurgical generator 12 reaches its maximum output voltage of e. g. 320 $V_{RMS}$, that the current intensity of the current supplied by the electrosurgical generator 12 decreases. However, this only happens at the very end of the vaporization phase—in the example shown in FIG. 6 e. g. at a degree of coverage of approximately 0.9 (90%).

The current density that increases because of the increasing degree of coverage causes the electroconductive fluid that is in contact with the active electrode 22 to heat up faster and faster, which can result in sudden, almost explosive vaporizations, as shown in FIG. 5c.

Figure 7:
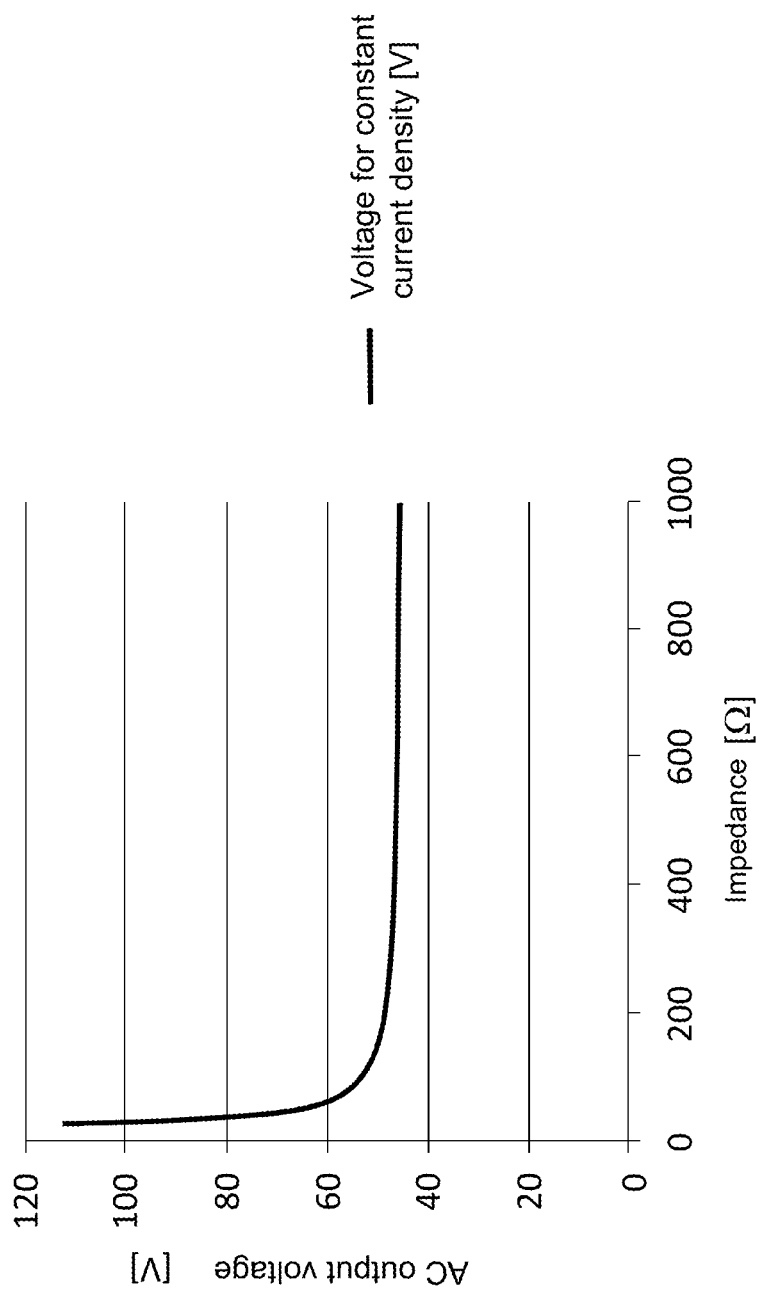
FIG. 7: A possible ideal development of a maximum output voltage value during the vaporization phase, controlled depending on the impedance detected during the vaporization phase.

This is an undesirable behavior that can negatively impact reliable and fast plasma ignition. The invention thus stipulates that, during the vaporization phase, the maximum output voltage of the electrosurgical generator 12 must be decreased below a value that is intended as the maximum output voltage value for the later equilibrium phase. This is accomplished by setting a maximum output voltage value for the vaporization phase in such a way that the maximum output voltage of the electrosurgical generator 12 is correspondingly low. Ideally, the maximum output voltage value for the maximum output voltage of the electrosurgical generator 12 is updated according to the degree of coverage, so that the maximum output voltage is initially higher with a lower degree of coverage and then decreases as the degree of coverage increases, so that the current intensity generated by the output voltage of the electrosurgical generator 12 decreases inversely proportionally to the degree of coverage of the electrode, and a nearly constant current density is achieved as a result. Since it is virtually impossible to directly determine or measure the degree of coverage sc, according to a preferred embodiment, the impedance between the outputs 18.1 and 18.2—which, as explained before, depends on the degree of coverage sc—is used to establish and update a suitable maximum output voltage value during the vaporization phase. FIG. 7 shows how, in the example described here, the maximum output voltage value can depend on the impedance measured between outputs 18.1 and 18.2 so that a constant current density is achieved during the entire vaporization phase based on the aforementioned assumptions (impedance of approximately 15Ω of the conductive fluid).

According to an alternative embodiment, the maximum output voltage value is not continuously updated depending on the degree of coverage or, alternatively, depending on the measured impedance, but specified as a constant value for the vaporization phase, while the vaporization phase is still detected based on the present impedance value.

Figure 6:
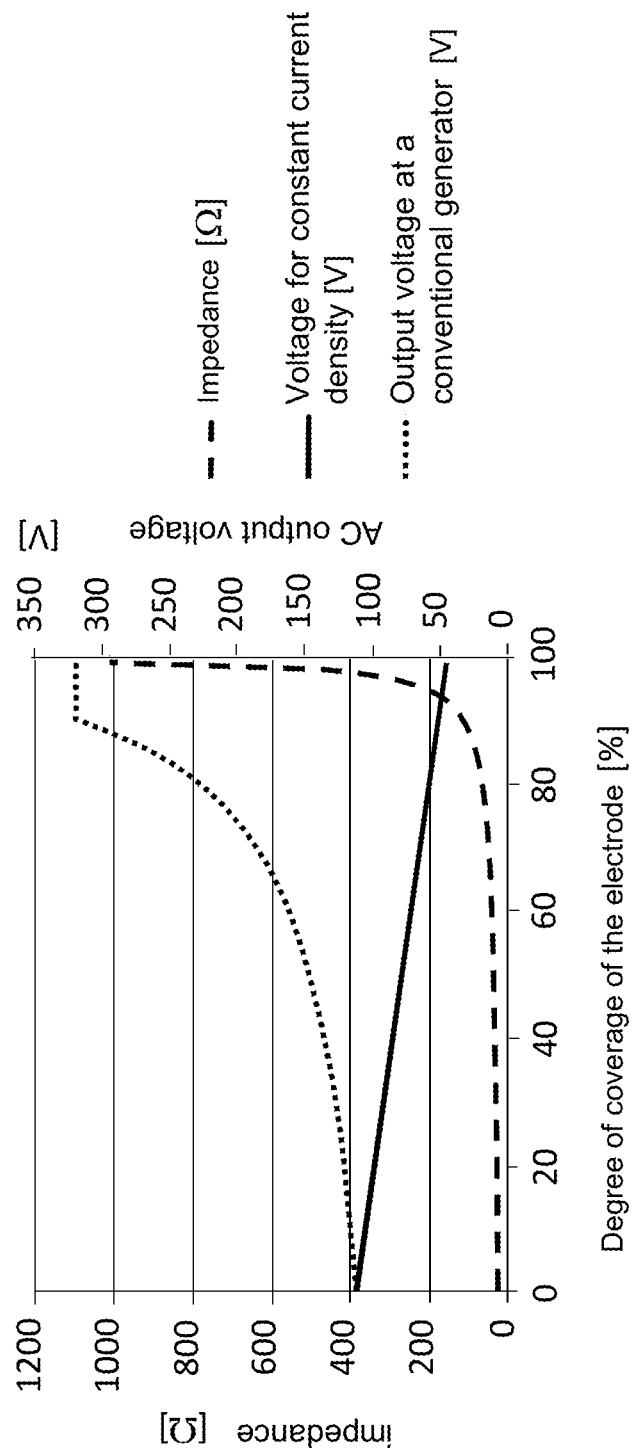
FIG. 6: A diagram to illustrate the voltage and impedance curves during the vapor and ignition phases when an arc is formed at the active electrode of the electrosurgical instrument.

It should be pointed out that FIG. 6 shows an example of an ideal curve of the AC output voltage during the vaporization phase as a function of the degree of coverage, namely the red line in FIG. 6. The RMS value of the AC output voltage at the start of the vaporization phase is thus between 110 and 120 V, and towards the end of the vaporization phase barely 50 V. Alternatively, it is also possible to predefine a constant RMS value for the AC output voltage of the electrosurgical generator 12 during the vaporization phase, where this constant value can be between e. g. 50 and 120 V, or better yet between 80 and 100 $V_{RMS}$.

As also explained above, the plasma around the active electrode 22 causes a DC offset (also referred to as spark voltage) in the AC output voltage of the electrosurgical generator 12 as soon as the plasma is ignited. Accordingly, successful ignition of the plasma can be identified based on the occurrence of a DC offset in the AC output voltage of the electrosurgical generator 12.

The end of the vaporization phase and thus the start of the ignition phase is preferably determined based on an impedance increase beyond an impedance value defined at the beginning of the vaporization phase and a detection impedance value based on a predefined factor or based on a drop in the AC output current below a predefined fraction of an AC output current value set at the beginning of the vaporization phase. When the start of the ignition phase is detected, the AC output voltage of the electrosurgical generator 12 is increased to the highest possible degree that is greater than the AC output voltage intended for the later equilibrium phase. This way a safe ignition of the arc is guaranteed. As soon as a first arc is produced—and thus a DC offset in the AC output voltage of the electrosurgical generator 12 is also detected—it is desirable that the AC output voltage of the electrosurgical generator 12 is maintained at the elevated AC output voltage value, which is greater than the AC output voltage intended for the later equilibrium phase, for a specific time. The specific time during which the AC output voltage of the electrosurgical generator 12 is to be maintained at the elevated AC output voltage value can be, for example, 10 to 80 ms or 40 to 60 ms.

Correspondingly, according to a preferred embodiment, it is intended that the output voltage control unit increases the maximum output voltage value to a value that is higher than the voltage value intended for the equilibrium phase. For example, the output voltage value intended for the equilibrium phase is between 250 $V_{RMS}$ and 320 $V_{RMS}$. The increased AC output voltage value can be e. g. 300 $V_{RMS}$ to 350 $V_{RMS}$. The result of an output voltage of the electrosurgical generator 12 thus increased during the ignition phase is that the arc is maintained as reliably as possible until the plasma in the vapor bubble around the active electrode 22 has stabilized. As soon as this occurs—and the equilibrium phase mentioned earlier then starts—the output voltage of the electrosurgical generator 12 can be decreased again by respectively lowering the maximum output voltage value for the output voltage control unit 36. This can be done gradually or abruptly. When the AC output voltage of the electrosurgical generator 12 is decreased after plasma ignition, the plasma layer (vapor bubble) around the active electrode 22 gets a little thinner; however, this does not result in the plasma being extinguished as long as the AC output voltage of the electrosurgical generator remains sufficiently high, for example, at 280 to 300 V.

In a simple exemplary embodiment, the electrosurgical generator 12 and its output voltage control unit 36 can be designed in such a way that the electrosurgical generator 12 initially provides a maximum AC output voltage between 100 and 200 V long enough until a DC voltage measuring unit detects a DC offset in the AC output voltage of the electrosurgical generator 12 that is greater than e. g. 50Ω. As soon as this DC offset is detected in the AC output voltage of the electrosurgical generator 12, the output voltage control unit 36 switches to a different maximum output voltage value of e. g. 320 V to stabilize the plasma during the ignition phase. The increased maximum output voltage value for the ignition phase can be reduced again after a predefined time, for example 10 to 50 ms, to a slightly lower value for the AC output voltage, for example to a maximum output voltage value between 250 and 300 $V_{RMS}$.

With this type of electrosurgical generator 12, it is possible to ignite plasma around an active electrode 22 reliably, and less dependent on the ambient parameters, within a short time span that does not fluctuate too much. This makes it a lot easier for a surgeon to use a respective electrosurgical system 10.

Figure 8:
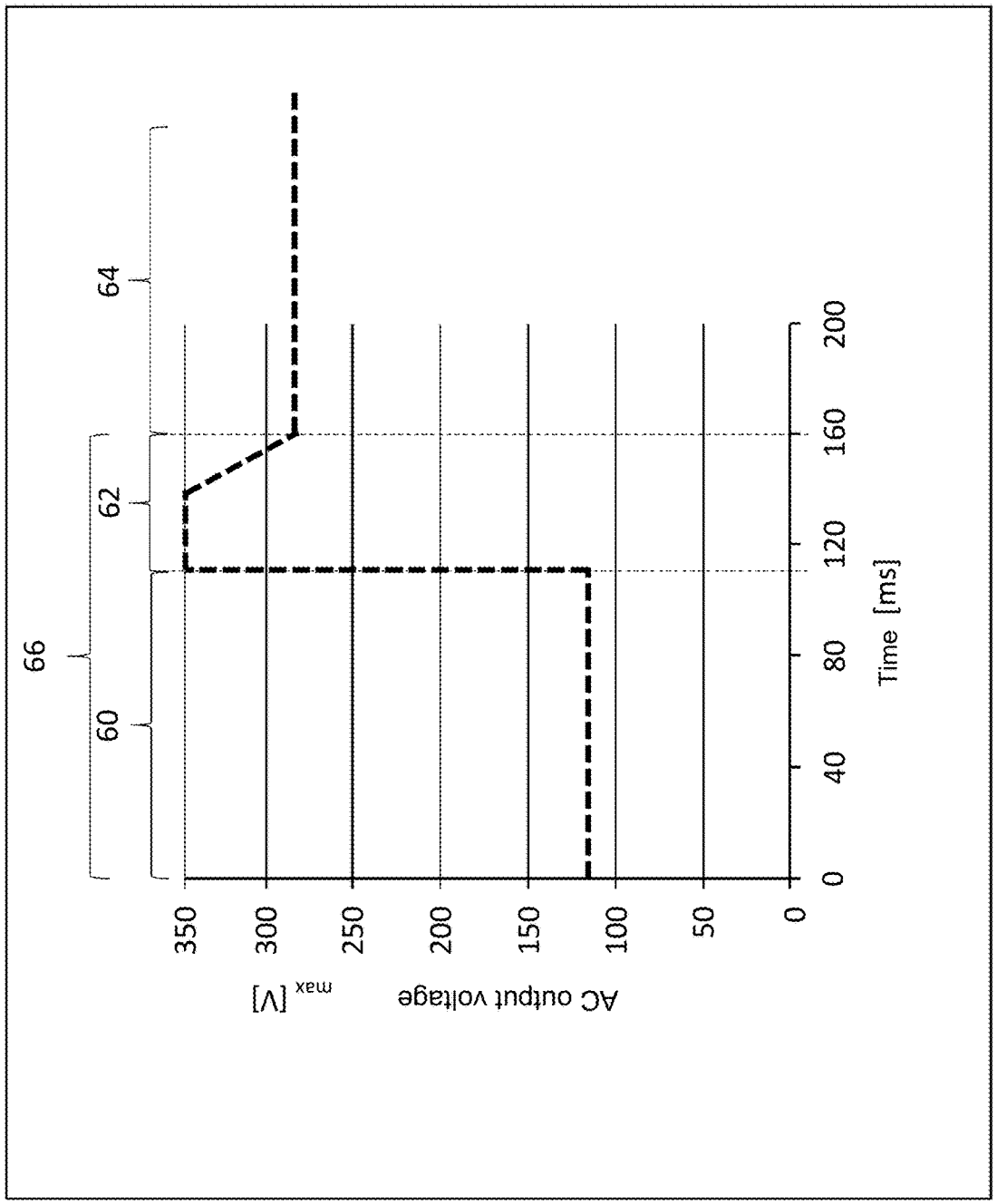
FIG. 8: A possible simplified development of a maximum output voltage value during the vaporization phase, the ignition phase, and the equilibrium phase.

FIG. 8 shows a possible simplified curve of a maximum output voltage value during the vaporization phase 60, the ignition phase 62, and the equilibrium phase 64. During the vaporization phase 60, for example, the maximum output voltage value is 100 $V_{RMS}$ or 120 $V_{RMS}$. At the beginning of the ignition phase 62, the maximum output voltage value is then increased to e. g. 300 $V_{RMS}$ or 350 $V_{RMS}$. After the ignition phase 62 ends, the maximum output voltage value is then decreased to the maximum output voltage value of e. g. 280 $V_{RMS}$ or 320 $V_{RMS}$ predefined for the equilibrium phase 64. The vaporization phase 60 and the ignition phase 62 together constitute the initial phase 66, during which the maximum output voltage value is either smaller or greater than during the subsequently occurring equilibrium phase 64.

The invention claimed is:

1. A method of operating an electrosurgical generator, wherein the method comprising:
   generating an AC output voltage and supplying the AC output voltage to outputs of the electrosurgical generator, wherein a maximum AC output voltage value is predefined for the AC output voltage;
   determining a load present at the outputs and comparing the load with a threshold value, which is defined such that a load falling below this threshold value indicates an occurrence of a vaporization phase;
   wherein, as long as the load remains below the threshold value, a maximum AC output voltage value is preset such that the maximum AC output voltage value is lower than a preset maximum output voltage value that is set when the threshold value is exceeded;
   controlling the AC output voltage based on the preset maximum AC output voltage value;
   establishing a vapor bubble as part of a vaporization phase during an initial phase;
   creating arcing as part of an ignition phase during the initial phase; and
   during the initial phase, applying the maximum AC output voltage value; and
   if the threshold value is exceeded, applying the preset maximum output voltage value that is higher than the maximum AC output voltage value.

2. The method of operating an electrosurgical generator according to claim 1, wherein the maximum AC output voltage value is updated depending on a specific load in a changing load, as long as the specific load remains below the threshold value.

3. A method of operating an electrosurgical generator, wherein the method comprising:
   generating an AC output voltage and supplying the AC output voltage to outputs of the electrosurgical generator, wherein a maximum AC output voltage value is predefined for the AC output voltage;
   determining a load present at the outputs and comparing the load with a threshold value, which is defined such that a load falling below this threshold value indicates occurrence of a vaporization phase;
   determining a DC offset in the AC output voltage present at the outputs,
   wherein, as soon as the threshold value is exceeded and a DC offset is not detected in the AC output voltage present at the outputs, a maximum AC output voltage value is preset such that the maximum AC output voltage is higher than a preset maximum output voltage value, the preset maximum output voltage value being preset if a DC offset is detected; and
   controlling the AC output voltage based on the maximum AC output voltage value;
   establishing a vapor bubble as part of a vaporization phase during an initial phase;
   creating arcing as part of an ignition phase during the initial phase; and
   during the initial phase, applying the maximum AC output voltage value; and
   if the DC offset is not detected, applying the preset maximum output voltage value that is higher than the maximum AC output voltage value.

4. Electrosurgical generator that is configured to implement a method according to claim 1, and to supply, during operation, a high-frequency alternating current to an electrosurgical instrument for plasma cutting of body tissue, wherein the electrosurgical generator has outputs for connecting an electrosurgical instrument to supply an electrosurgical instrument connected to the outputs during operation with a high-frequency alternating current, and for determining an impedance of a load connected to the outputs;
   wherein the electrosurgical generator further features an impedance measuring unit and a voltage measuring unit as well as an output voltage control unit, of which
   the output voltage control unit is configured to control or regulate an AC output voltage of the electrosurgical generator in accordance with a predefined maximum output voltage value, and
   the impedance measuring unit is designed to determine an impedance of the load present at the outputs of the electrosurgical generator during operation;
   wherein:
   the output voltage control unit is designed to control the AC output voltage depending on a maximum output voltage value which, at least for part of an initial phase, is a different maximum output voltage value than during a subsequently occurring equilibrium phase.

5. Electrosurgical generator according to claim 4, wherein the output voltage control unit is designed to control the AC output voltage depending on a maximum output voltage value that is set as a function of an output value during operation, such that the maximum output voltage value during the vaporization phase is lower than the maximum output voltage value during a later equilibrium phase.

6. Electrosurgical generator according to claim 4, wherein the output voltage control unit is designed to control the AC output voltage depending on a maximum output voltage value that is set during operation depending on an output value of the impedance measuring unit and/or depending on an output value of the voltage measuring unit, such that the maximum output voltage value is higher during an ignition phase than the maximum output voltage value during an equilibrium phase occurring subsequently to the ignition phase.

7. Electrosurgical generator according to claim 6, wherein the electrosurgical generator is designed to detect an end of the ignition phase based on a DC offset in the voltage present at the outputs of the electrosurgical generator.

8. Electrosurgical generator according to claim 4, wherein the electrosurgical generator is designed to detect the vaporization phase based on a measured impedance.

9. Electrosurgical generator according to claim 8, wherein the electrosurgical generator is designed to detect an end of the vaporization phase based on an impedance increase at the outputs of the electrosurgical generator beyond a predefined value, wherein the predefined value is derived from the impedance measured by the impedance measuring unit at a start of the vaporization phase.

10. Electrosurgical generator according to claim 4, wherein the output voltage control unit is designed to apply, during the vaporization phase, a maximum output voltage value updated depending on a respectively current output value of the impedance measuring unit and/or the voltage measuring unit.

11. Electrosurgical generator according to claim 4, wherein the output voltage control unit is designed to apply, during the vaporization phase, a maximum output voltage value that is predefined for the vaporization phase.

12. Electrosurgical generator according to claim 4, wherein the electrosurgical generator is dimensioned in such a way that it can supply a maximum AC output voltage of more than 300 V and a maximum AC output current of more than 4 A.

13. Electrosurgical system with an electrosurgical generator according to claim 4, and with an electrosurgical instrument that is or can be connected to outputs of the electrosurgical generator, and that has an active electrode and at least one return electrode as well as at least one fluid line that is arranged relative to the active electrode in such a way that the active electrode can be surrounded by an electroconductive fluid during operation.

14. Electrosurgical system according to claim 13, wherein the active electrode is designed as a loop electrode or a button electrode.

15. Electrosurgical system according to claim 13, wherein the electrosurgical instrument is a resectoscope.

* * * * *